United States Patent [19]

Brändle et al.

[11] Patent Number: 5,421,190
[45] Date of Patent: Jun. 6, 1995

[54] DEVICE FOR MEASURING GAS DENSITY

[75] Inventors: Hubert Brändle, Otelfingen; Walter Gribi, Wettingen; Ken-Yves Haffner, Baden, all of Switzerland

[73] Assignee: Asea Brown Boveri Ltd., Baden, Switzerland

[21] Appl. No.: 70,948

[22] Filed: Jun. 4, 1993

[30] Foreign Application Priority Data

Jun. 10, 1992 [DE] Germany .................. 42 18 926.8

[51] Int. Cl.⁶ .................. G01H 13/00; H01L 41/22
[52] U.S. Cl. .................. 73/30.01; 73/580; 73/24.05
[58] Field of Search .................. 73/24.06, 24.05, 30.01, 73/31.05, 580

[56] References Cited

U.S. PATENT DOCUMENTS

| | | | |
|---|---|---|---|
| 4,446,720 | 5/1984 | Sinclair | 73/24.06 |
| 4,561,286 | 12/1985 | Sekler et al. | 73/24.06 |
| 4,734,609 | 3/1988 | Jasmine | 73/24.05 X |
| 5,191,795 | 5/1993 | Fellingham et al. | 73/599 |

FOREIGN PATENT DOCUMENTS

| | | | |
|---|---|---|---|
| 538235 | 7/1981 | European Pat. Off. | 73/30.01 |
| 0101669A2 | 2/1984 | European Pat. Off. | |
| 0484569A1 | 5/1992 | European Pat. Off. | |
| 3537386A1 | 4/1987 | Germany | |
| 56-86331 | 7/1981 | Japan | 73/30.01 |

OTHER PUBLICATIONS

Panin, I. A., "Vibrational, Gas Densitometers", Measurement Techniques, vol. 18, No. 7, (USSR transl.) Plenum Publishing Corporation, Jul. 1975, pp. 1090–1092.

*Primary Examiner*—Hezron E. Williams
*Assistant Examiner*—David Wiggins
*Attorney, Agent, or Firm*—Burns, Doane, Swecker & Mathis

[57] ABSTRACT

The device serves to measure the density of a gas, in particular of the insulating gas of a gas-insulated electrical installation. It contains two resonators (11, 12) each comprising a piezoelectric crystal (14, 15) and each comprising two electrodes applied to the crystal. A first (11) of the two resonators (11, 12) is mounted in a first chamber (5) containing the gas to be measured, whereas a second (12) is mounted in a second chamber (6) sealed with respect to the gas.

Despite small dimensions and despite simple and robust construction, this device is intended to have a high measurement precision over a long period of time.

This is achieved by drawing the two resonators (11, 12) from a multiplicity of similar resonators manufactured by mass production and not subjected to a frequency alignment. The first resonator (11) is unaltered with respect to the manufacture in mass production. The second resonator (12) is likewise unaltered with respect to the manufacture in mass production and, under vacuum and with equality of temperature, it has the same resonance frequency as the first resonator (11) within a specified frequency tolerance. The second resonator (12) may, however, also be modified, by altering its electrodes (18, 19), in such a way that, under vacuum and with equality of temperature, it has the same resonance frequency as the first resonator (11) within the specified frequency tolerance.

16 Claims, 3 Drawing Sheets

DEVICE FOR MEASURING GAS DENSITY

BACKGROUND OF THE INVENTION

1. Field of the Invention

The invention proceeds from a device for measuring the density of a gas, in particular of the insulating gas of a gas-insulated electrical installation, comprising two resonators each containing a piezoelectric crystal and each containing at least two electrodes applied to the crystal, of which two resonators a first is mounted in a first chamber containing gas to be measured and a second is mounted in a second chamber sealed with respect to the gas. The invention furthermore proceeds from methods of producing a gas-density measuring device of this type.

2. Discussion of Background

A device of the type mentioned in the introduction is described in EP-A-0 484 569. In the case of this device, the density of sulfur hexafluoride in a gas-insulated electrical high-voltage installation is measured by means of two resonators. For identical external conditions, i.e. at a predetermined temperature and with the same environment, such as, in particular, vacuum, both resonators have identical resonance frequencies. One of the two resonators serves as sensor and is disposed in a chamber containing sulfur hexafluoride. The gas-density-dependent detuning of its resonance frequency is in this case a measure of the density of the sulfur hexafluoride to be measured. Another of the two resonators is provided for reference purposes and is preferably disposed under vacuum. A measured signal which is proportional to the density of the sulfur hexafluoride is tapped off in an evaluating electronic system to which the output signals of the two resonators are applied.

In this case, piezoelectrically excited tuning-fork crystals are used as resonators. These crystals are cut out of a quartz wafer in large numbers in the clock industry in the production of timepieces and are each coated with two gold electrodes. These gold electrodes serve, on the one hand, for the piezoelectric excitation of the tuning-fork crystal with the aid of an electrical oscillatory circuit. On the other hand, they also serve, however, to tune the individual tuning-fork crystals to a standard fundamental resonance frequency of 32,768 Hz at a temperature of 25° C.

SUMMARY OF THE INVENTION

Accordingly, one object of the invention as defined in patent claims 1, 8 and 9 is to provide a novel device of the type mentioned in the introduction which, despite small dimensions and despite simple and robust construction, has a high measurement precision over a long period of time, and at the same time to provide methods with the aid of which said device can be inexpensively produced.

The device according to the invention enables a high-precision measurement of the gas density up to high values, for example of 50 kg/m$^3$ and over. The density measurement is largely independent of the temperature and also provides values which are uniformly exact over very long periods of time. For this reason the device according to the invention is suitable, with particular advantage, for continuously monitoring and for diagnosing installations which are operated for a long time and also for determining trends in gas losses which may commence. The maintenance of installations operated for a long time can thus be economically planned and performed. Possible sources of error may, in addition, be located in good time and eliminated. The availability of the installations monitored for gas density is consequently increased appreciably.

Methods in accordance with the invention which are particularly suitable for producing devices according to the invention are notable for the fact that they are eminently suitable for mass production. Expensive calibration and adjustment operations are largely unnecessary since all the resonators used for the gas-density measuring devices to be produced have mutually equivalent frequency/density characteristic curves within a specified tolerance range.

The advantageous effects of the invention are based primarily on the discovery that unwanted frequency anomalies are avoided virtually completely by systematic use of similarly constructed and similarly operating resonators. On the other hand, such frequency anomalies occur if, for instance (as hitherto usual), a part of the electrode material provided to excite the resonators has to be removed by means of a laser during the tuning of all the resonators produced by mass production to a standard resonance frequency. As a result, the resonator disposed in the gas not only undergoes the desired density-dependent resonance shift but also unwanted frequency shifts which are dependent on the temperature, the viscosity of the gas and the interaction of the resonator with the sound waves produced during resonance.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
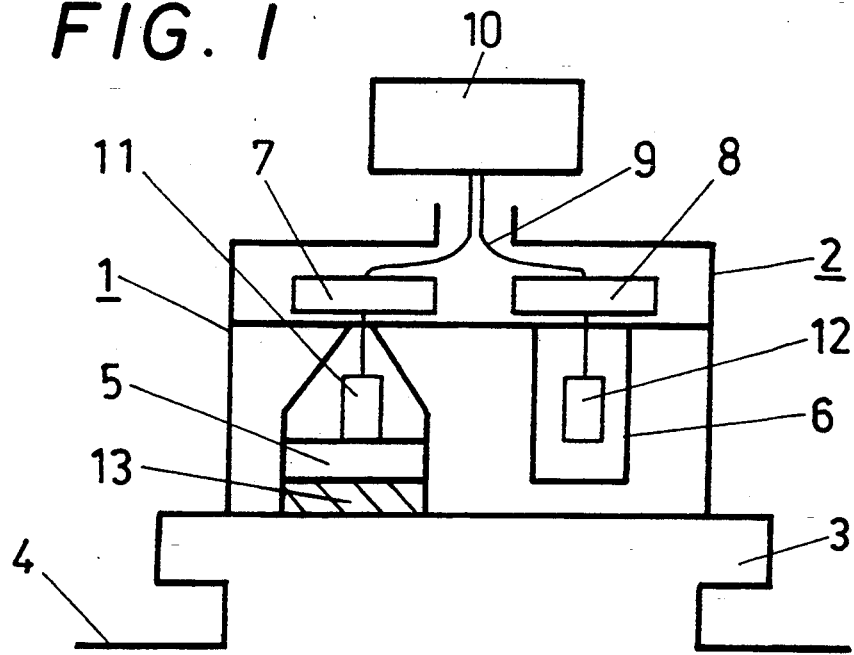
FIG. 1 shows a view of a section through a part of a gas-insulated encapsulated switching installation having a gas-density measuring device according to the invention.

Referring now to the drawings, wherein like reference numerals designate identical or corresponding parts throughout several views, in FIG. 1 a gas-density measuring device having a sensor head 2 is denoted by 1. The sensor head 2 closes, by means of a gastight joint 3, an opening, which is not shown, of a metal encapsulation 4 of an electrical installation constructed, for instance, as a high-voltage switching installation, which metal encapsulation 4 is filled with sulfur hexafluoride (SF$_6$) gas at a pressure of, for example, a few kg.m$^{-2}$. The sensor head 2 contains two chambers 5 and 6 which are gastightly partitioned with respect to one another. The reference numerals 7 and 8 denote an electrical oscillatory circuit. The supply energy of the oscillatory circuits 7, 8 is drawn from a current source, which is not shown. The output signals of the oscillatory circuits are fed via connecting leads, which are not shown, and a leadthrough 9 to an evaluating device 10 in which a signal indicating the gas density of the SF$_6$ gas contained in the metal encapsulation 4 is determined and outputted to an observer and/or a monitoring device.

The oscillatory circuit 7 contains a resonator 11 which is disposed in the chamber 5 and exposed to the SF$_6$ gas, whereas the oscillatory circuit 8 contains a resonator 12 which is exposed to known pressure conditions, preferably vacuum, in the chamber 6 with the SF$_6$ atmosphere being excluded. The chamber 5 is connected to the interior of the metal encapsulation 4 via an opening, which is not shown. Situated in the connecting opening is a filter arrangement 13 which protects the resonator 11 against mechanical damage and which at the same time adsorbs decomposition products of the SF$_6$ gas formed in the interior of the metal encapsulation 4 during electrical discharging, but allows through undecomposed SF$_6$ gas or, possibly, another insulating gas additionally provided, such as, for instance, nitrogen.

Figure 2:
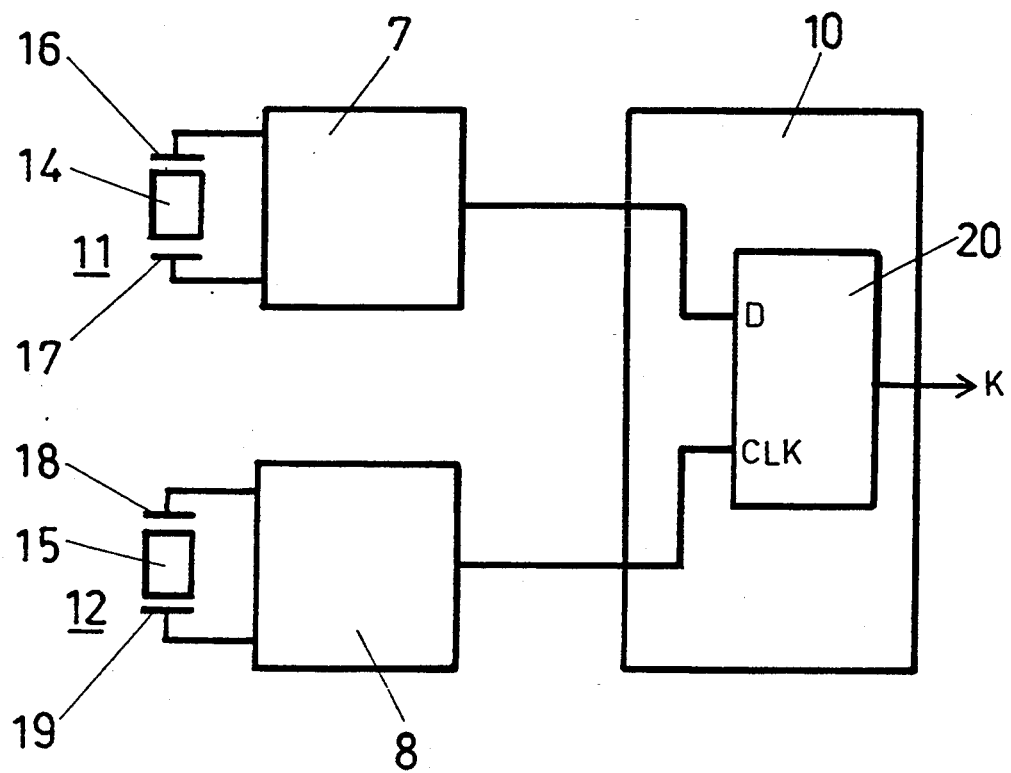
FIG. 2 shows a block circuit diagram of the measuring device shown in FIG. 1.

The resonators 11, 12 are piezoelectrically excited and have resonance frequencies located within a specifiable frequency tolerance (of, for example, 1 or 2 Hz). As can be seen from FIG. 2, the resonators 11, 12 each contain a piezoelectric crystal 14, 15 and they each contain at least two electrodes 16, 17, 18, 19 applied to the piezoelectric crystal 14, 15. Preferably, the piezoelectric crystals, 14, 15 are tuning-fork crystals which can each be caused to oscillate by an alternating voltage applied to their electrodes 16, 17, 18, 19. The surrounding gas increases the effective mass of the resonator 11 and results in a density-dependent resonance displacement. The relationship between density change and frequency displacement is essentially linear. In SF$_6$, this displacement is, for example, approximately $-4.7$ Hz/kg.m$^{-3}$.

The resonators 11, 12 are drawn from a multiplicity of resonators which are similar with respect to their physical properties and their geometrical dimensions and are manufactured by mass production. The first resonator 11 is unaltered with respect to the manufacture in mass production. The second resonator 12 may likewise be unaltered with respect to the manufacture in mass production and is selected in such a way that, under vacuum and with equality of temperature, it has the same resonance frequency as the first resonator 11 within a specified frequency tolerance. It may, however, also be modified, by altering its electrodes 18, 19, in such a way that, under vacuum and with equality of temperature, it has the same resonance frequency as the first resonator 11 within the specified frequency tolerance. The resonance frequency is typically in the region of approximately 32.6 kHz.

The oscillatory circuits 7 and 8, respectively are each preferably constructed as inverter circuits which supply rectangular pulses. Said rectangular pulses contain the information about the resonance frequencies of the resonators 11 and 12. As can be seen from FIG. 2, they are fed to the D input and the clock input CLK, respectively, of a D-flipflop 20 contained in the evaluating device 10. By correlating the signals supplied, the D-flipflop 20 generates a signal k corresponding to the difference in the resonance frequencies of the resonators 11, 12 and proportional to the gas density.

Figure 3:
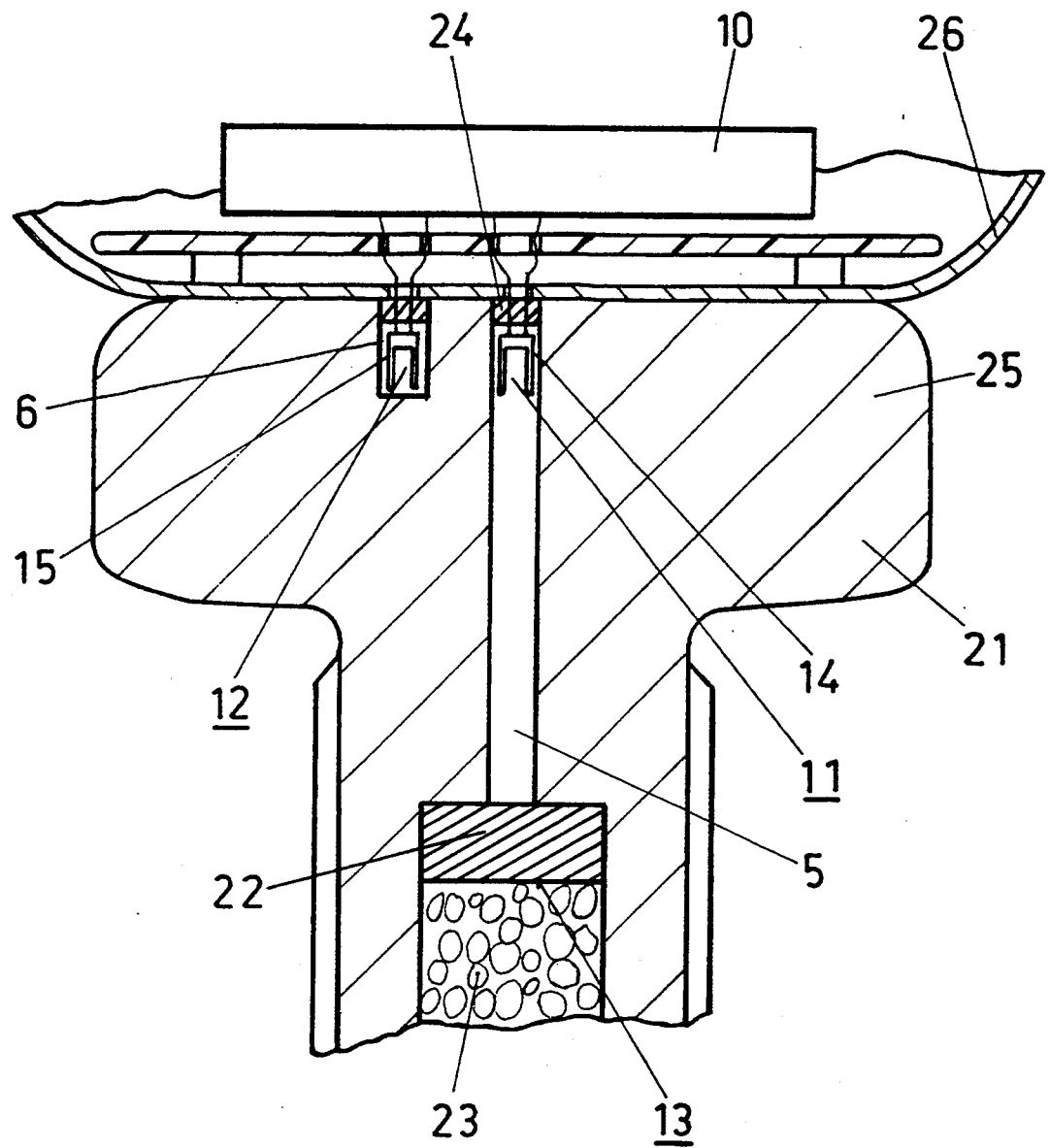
FIG. 3 shows a view of a section through a part of a first sensor head contained in the gas-density measuring device shown in FIG. 1.

The constructional arrangement of the resonators 11, 12 in the sensor head 2 is shown in FIG. 3. The sensor head 2 contains a mounting body 21 of rotationally symmetrical form which is made of thermally conducting material, such as, for example, brass, and has an axially and centrally routed bore. In its upper section, the bore forms the chamber 5 for receiving the resonator 11. In its lower section it provides the connection with the SF$_6$ gas provided in the metal encapsulation 4 and is filled at that point with the filter arrangement 13. The filter arrangement 13 comprises a porous sintered metal disk 22 which keeps solid particles possibly produced in the metal encapsulation 4 away from the chamber 5 and, consequently, also from the resonator 11, and an adsorption filter 23. Said adsorption filter 23 contains a tube filled with molecular sieve, active clay, soda asbestos, soda lime or a substance with a similar action.

Gaseous decomposition products such as, for instance, SF$_4$, WF$_6$, SOF$_2$ and/or HF, formed as a result of electrical discharges and residual humidity during the operation of the high-voltage switching installation are absorbed by the adsorption filter 23. The chamber 5 and, consequently, also the resonator 11 remain free of unwanted decomposition products of this type which appreciably impair the operation of the resonator 11, while the gas to be measured reaches the chamber 5 and, consequently, the resonator 11 in pure form.

The chamber 5, which receives the resonator 11, is constructed in such a way that acoustic interactions with the surroundings of the resonator 11 are largely avoided. This can be achieved, on the one hand, by the chamber 5 being made large compared with the wavelength of a sound wave radiated by the resonator 11 into the gas to be measured at resonance frequency.

Frequently, such a large chamber is not available. It is then advisable to design the chamber 5 so that no interferences can affect the wanted signal. An axially symmetrical, in particular cylindrically symmetrical, construction is to be preferred. The diameter of the chamber 5 should in this case be less than half the wavelength of a sound wave radiated by the resonator 11 into the gas to be measured at (fundamental) resonance frequency.

The acoustic interaction of the resonator 11 constructed as tuning-fork crystal is additionally reduced if the tuning-fork crystal is disposed with its tuning-fork axis on the axis of the cylindrical chamber 5 receiving it.

The chamber 5 is gastightly sealed at its upper end with a leadthrough 24 which routes the electrical connections of the electrodes of the resonator 11 out of the chamber 5 and into a housing 26 enclosing the evaluating device 10 and mounted on a flange 25 of the mounting body 21. The resonator 11 is preferably mounted in the upper end of the chamber 5 by gluing or pressing in the leadthrough 24. The length of the chamber 5 suitable for avoiding acoustic interactions is then determined by the distance between the open end of the chamber 5 and the freely vibrating ends of the quartz tuning fork of the resonator 11.

The chamber 6, which receives the resonator 12 provided for comparison purposes, is constructed as a blind bore and is disposed in close proximity to the chamber 5 in the mounting body 21. The two resonators 11, 12 are kept at the same temperature by the local proximity of the two resonators 11, 12 and by the good heat conduction of the mounting body 21, of the sulfur hexafluoride and of a heat-conducting grease which may be used. As a result, and since the two resonators 11, 12 have geometrical dimensions which are matched within a specified tolerance range and have matching physical properties, resonance frequency changes due to temperature are compensated for within the specified frequency tolerance.

Figure 4:
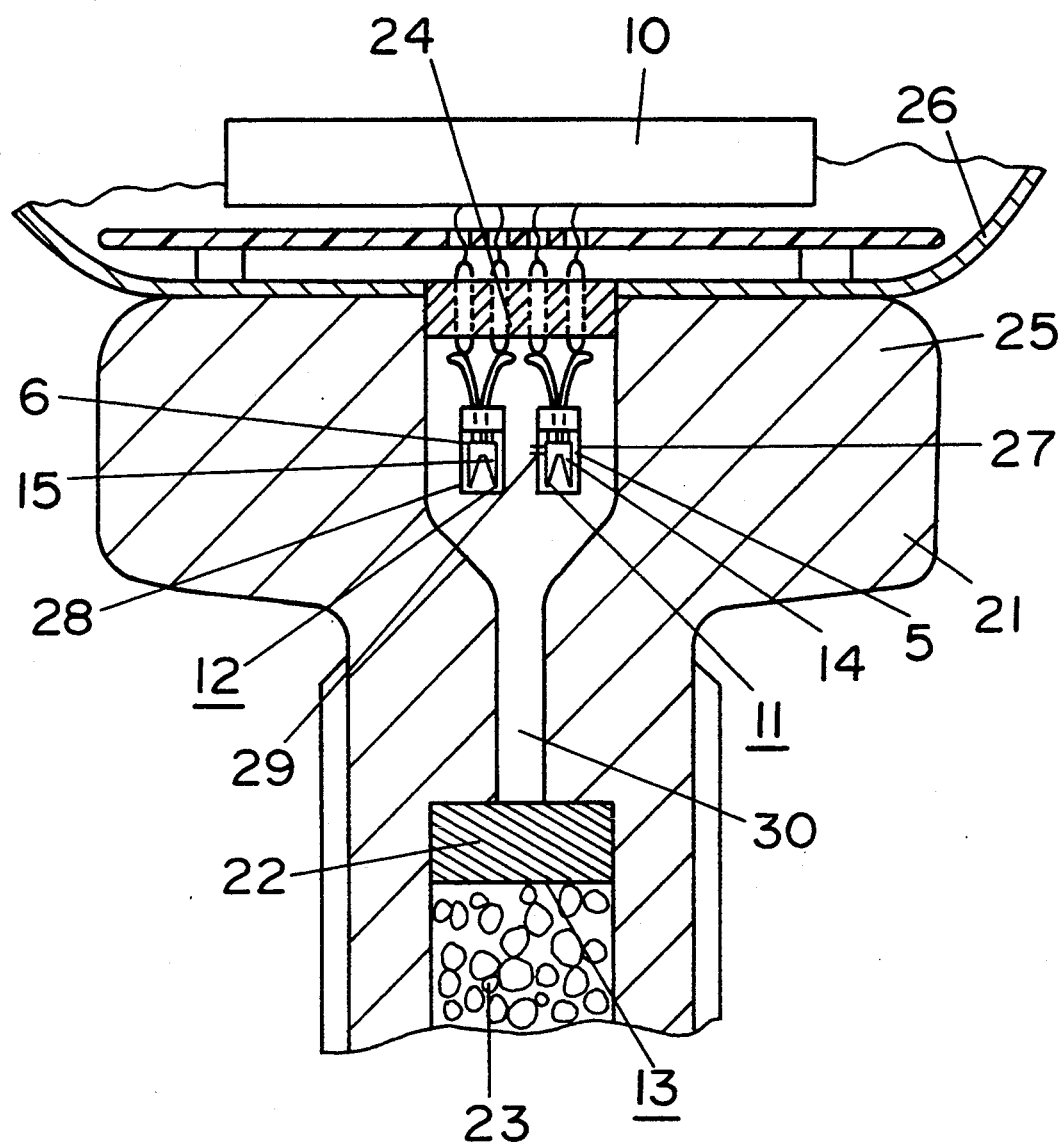
FIG. 4 shows a view of a section through a part of a second sensor head contained in the gas-density measuring device shown in FIG. 1.

A particularly high measurement precision is achieved with a sensor head constructed as shown in FIG. 4. In this sensor head, the resonator 11 is disposed in a sleeve 27 manufactured during the mass production of the resonators 11, 12 and forming the boundary of the chamber 5, and the resonator 12 is disposed in a sleeve 28 likewise manufactured in the mass production of the resonators but forming the boundary of the chamber 6. The chamber 5 is connected via an opening 29 in the wall of the sleeve 27 to a chamber 30 which contains the gas to be measured and receives both the sleeves 27 and 28. The two sleeves 27, 28 are composed of metal, such as, for instance, German silver, and are each of cylindrical construction. Typically, they each have an inside diameter of approximately 1.6 mm and an inside height of approximately 5 mm. The opening 29 is formed by a lateral puncture having a diameter of, typically, approximately 0.2 mm. The two resonators 11, 12 comprise tuning-fork crystals as piezoelectric crystals 14, 15. These crystals are driven via electrical leads which are routed into the chamber 30 by means of a four-way glass leadthrough, for example a transistor mounting.

In this sensor head, the two resonators 11, 12 and the electrical leads are in good thermal contact with the gas to be measured in a very constricted space. Heat is therefore very rapidly exchanged, (moreover, the same amount in each case) between the gas and the two resonators 11, 12 and the electrical leads. Both resonators 11, 12 are therefore always at the same temperature, even during rapid heating or cooling of the gas to be measured. The precision of such a gas-density measurement is in the per mil range.

Before being mounted in the sensor heads 2 shown in FIGS. 3 and 4, the two resonators 11, 12 are selected from a multiplicity of resonators which are similar to one another in respect of their physical properties and their geometrical dimensions. For this purpose, their resonance frequencies are determined under identical measurement conditions and that pair of resonators is selected whose resonance frequencies are within the specified frequency tolerance, which is dependent on the measurement sensitivity to be achieved. Further pairs of resonators with matching resonance frequencies are selected from the multiplicity of resonators, available for selection, for mounting in further gas-density measuring devices according to the invention.

Preferably, the piezoelectric crystals 14, 15 provided in the resonators 11, 12 and all the other crystals provided in the multiplicity of similar resonators are produced from a single quartz wafer corresponding to the thickness of the tuning fork (for example 125 $\mu$m) or from a batch of wafers from the same quartz-crystal block. The necessary matching of the geometrical dimensions and of the physical properties is then achieved with particularly high reliability. About 200 tuning-fork crystals can typically be produced from a single quartz wafer. The statistical spread of the resonance frequencies of the oscillators produced from these tuning-fork crystals is ±180 Hz. Resonators produced from the same wafer or from a batch of identical wafers are notable for the fact that they have a virtually identical resonance frequency temperature response.

In addition to the selection of suitably constructed pairs of resonators, a gastight measuring device according to the invention can also be advantageously achieved by taking any desired pair of resonators from a multiplicity of resonators comprising piezoelectric crystals 14, 15 which are equivalent in respect of their material properties and by altering the resonator serving as reference (preferably disposed under vacuum) by machining, in particular by material-removing machining, in such a way that its resonance frequency matches the resonance frequency of the resonator disposed in the gas within the specified frequency tolerance.

The electrodes of the resonator 11 exposed to the gas must no longer be altered after application to the piezoelectric crystal 14. Only in this way is it reliably guaranteed that the resonator 11 compensates for the unwanted frequency anomalies which occur alongside the desired density-dependent resonance shift and which are dependent on the temperature, the viscosity of the gas and the interaction of the resonator 11 with the sound waves produced during resonance.

The invention is not used solely to measure the density of the insulating gas of electrical installations. It can be advantageously used to measure the density of gases wherever the density of the gas is measured and monitored over a long period of time with good precision.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of making a device for measuring density of a gas, said device comprising two resonators having resonant frequencies located within a specified frequency tolerance, each of said resonators including a piezoelectric crystal and at least two electrodes applied to each piezoelectric crystal, a first of the two resonators being mounted in a first chamber wherein the gas to be measured is input, and a second of the two resonators being mounted in a second chamber which is sealed to prevent input of the gas, said method comprising, prior to the mounting of the two resonators, the steps of:

machining a multiplicity of piezoelectric crystals from a single crystal wafer or from a batch of wafers obtained from a crystal block, said multiplicity of piezoelectric crystals having physical properties and geometrical dimensions which are similar to one another;

applying electrodes to each piezoelectric crystal of the multiplicity of crystals for generating a multiplicity of resonators having a statistical spread of resonance frequencies which is greater than said frequency tolerance;

determining the resonance frequencies for plural resonators of the multiplicity of resonators using similar measuring conditions; and selecting said first and second resonators from said multiplicity of resonators based on said determined resonance frequencies.

2. The method according to claim 1, further including the step of:

mounting said first and second resonators adjacent one another in a thermally conductive mounting body.

3. The method according to claim 2, wherein said step of mounting further includes the step of:

gluing or pressing-in said first and second resonators into said mounting body to form a gas-tight seal.

4. The method according to claim 1, wherein said method of making said measuring device further includes the step of:

mounting said first and second resonators for measuring an insulating gas of a gas-insulated electrical installation.

5. The method according to claim 1, wherein said frequency tolerance is two Hertz or less.

6. A method of making a device for measuring density of a gas, said device comprising two resonators having resonant frequencies located within a specified frequency tolerance, each of said resonators including a piezoelectric crystal and at least two electrodes applied to each piezoelectric crystal, a first of the two resonators being mounted in a first chamber wherein the gas to be measured is input, and a second of the two resonators being mounted in a second chamber which is sealed to prevent input of the gas, said method comprising, prior to the mounting of the two resonators, the steps of:

machining a multiplicity of piezoelectric crystals from a single crystal wafer or from a batch of wafers obtained from a crystal block, said multiplicity of piezoelectric crystals having physical properties and geometrical dimensions which are similar to one another;

applying electrodes to each piezoelectric crystal of the multiplicity of crystals for generating a multiplicity of resonators having a statistical spread of resonance frequencies which is greater than said frequency tolerance;

determining the resonance frequencies for plural resonators of the multiplicity of resonators using similar measuring conditions;

selecting a pair of resonators from said multiplicity of resonators for use as said first and second resonators; and machining one of said selected first and second resonators to match its resonance frequency with the resonance frequency of the other of said first and second resonators within said frequency tolerance.

7. The method according to claim 6, wherein said step of machining one resonator of said selected pair includes the step of:

removing material used to form the electrodes of at least one of said two resonators.

8. The method according to claim 6, further including the step of:

mounting said first and second resonators adjacent to one another in a thermally conductive mounting body.

9. The method according to claim 8, wherein said step of mounting further includes the step of:

gluing or pressing-in said first and second resonators into said mounting body to form a gas-tight seal.

10. The method according to claim 6, wherein said method of making said measuring device further includes the step of:

mounting said first and second resonators for measuring an insulating gas of a gas-insulated electrical installation.

11. A method according to claim 6, wherein said frequency tolerance is two Hertz or less.

12. A device for measuring the density of gas, in particular of the insulating gas of a gas-insulated electrical installation, comprising:

two resonators each containing a piezoelectric crystal and each containing at least two electrodes applied to the crystal, of which two resonators a first is mounted in a first chamber containing gas to be measured and a second is mounted in a second chamber sealed with respect to the gas, wherein the two resonators are drawn from a multiplicity of similar resonators manufactured by mass production and not subjected to a frequency alignment, wherein the first resonator is unaltered with respect to the manufacture in mass production, and wherein the second resonator is likewise either unaltered with respect to the manufacture in mass production and, under vacuum and with equality of temperature, it has the same resonance frequency as the first resonator within a specified frequency tolerance or, alternatively, under vacuum and with equality of temperature, it has the same resonance frequency as the first resonator within the specified frequency tolerance after its electrodes have been altered, said first resonator being disposed in a first sleeve manufactured during mass production and forming the boundary of the first chamber, and the second resonator being disposed in a second sleeve manufactured during mass production and forming the boundary of the second chamber, the first chamber being connected via an opening in the wall of the first sleeve to a third chamber which contains the gas to be measured and which receives the first and the second sleeve, the first chamber being constructed such that acoustic interactions with the surroundings of the first resonator are largely avoided, and being large compared with the wavelength of a sound wave radiated by the first resonator into the gas to be measured at resonance frequency and/or wherein the first chamber has walls which absorb ultrasound.

13. A device for measuring the density of gas, in particular of the insulating gas of a gas-insulated electrical installation, comprising two resonators each containing a piezoelectric crystal and each containing at least two electrodes applied to the crystal, of which two resonators a first is mounted in a first chamber containing gas to be measured and a second is mounted in a second chamber sealed with respect to the gas, wherein the two resonators are drawn from a multiplicity of similar resonators manufactured by mass production and not subjected to a frequency alignment, wherein the first resonator is unaltered with respect to the manufacture in mass production, and wherein the second resonator is likewise either unaltered with respect to the manufacture in mass production and, under vacuum and with equality of temperature, it has the same resonance frequency as the first resonator within a specified frequency tolerance or, alternatively, under vacuum and with equality of temperature, it has the same resonance frequency as the first resonator within the specified frequency tolerance after its electrodes have been altered, said first resonator being disposed in a first sleeve manufactured during mass production and forming the boundary of the first chamber, and the second resonator being disposed in a second sleeve manufactured during mass production and forming the boundary of the second chamber, the first chamber being connected via an opening in the wall of the first sleeve to a third chamber which contains the gas to be measured and which receives the first and the second sleeve, the first chamber being constructed such that acoustic interactions with the surroundings of the first resonator are largely avoided, and being of axially symmetrical, in particular cylindrical, construction, wherein the diameter of the first chamber is less than half the wavelength of a sound wave radiated by the first resonator into the gas to be measured at resonance frequency.

14. The device according to claim 13, wherein the two resonators each include a tuning-fork crystal as the piezoelectric crystal, and wherein the tuning-fork crystal of the first resonator is disposed axially symmetrically in the chamber.

15. The method according to claim 1, wherein said specified frequency tolerance is 2 Hertz or less.

16. The method according to claim 6, wherein said specified frequency tolerance is 2 Hertz or less.

* * * * *